(12) United States Patent
Carlisle et al.

(10) Patent No.: US 7,895,882 B2
(45) Date of Patent: Mar. 1, 2011

(54) DENSITY ANALYSIS FOR FLOW SENSOR-BASED FLUID CONTROL SYSTEM

(75) Inventors: Jeffrey A. Carlisle, Stratham, NH (US); Benjamin G. Powers, Portsmouth, NH (US)

(73) Assignee: Fluidnet Corporation, Amesbury, MA (US)

( * ) Notice: Subject to any disclaimer, the term of this patent is extended or adjusted under 35 U.S.C. 154(b) by 271 days.

(21) Appl. No.: 12/206,502

(22) Filed: Sep. 8, 2008

(65) Prior Publication Data

US 2009/0229374 A1   Sep. 17, 2009

Related U.S. Application Data

(63) Continuation-in-part of application No. 12/048,612, filed on Mar. 14, 2008.

(51) Int. Cl.
*G01N 9/32* (2006.01)

(52) U.S. Cl. .......................................... 73/32 R

(58) Field of Classification Search .................. 73/32 R; 604/132
See application file for complete search history.

(56) References Cited

U.S. PATENT DOCUMENTS

| | | | |
|---|---|---|---|
| 4,090,514 A | 5/1978 | Hinck et al. | 604/142 |
| 4,191,184 A | 3/1980 | Carlisle | 604/153 |
| 4,470,758 A | 9/1984 | Pazemenas et al. | |
| 4,539,005 A | 9/1985 | Greenblatt | 604/141 |
| 4,561,298 A | 12/1985 | Pond | 73/149 |
| 4,976,162 A | 12/1990 | Kamen | 73/865.9 |
| 5,207,645 A | 5/1993 | Ross et al. | 604/141 |
| 5,308,335 A | 5/1994 | Ross et al. | 604/141 |
| 5,348,539 A | 9/1994 | Herskowitz | 604/141 |
| 5,433,704 A | 7/1995 | Ross et al. | 604/67 |
| 5,464,391 A | 11/1995 | DeVale | 604/67 |
| 5,533,381 A | 7/1996 | Seale | 73/19.03 |
| 5,554,123 A | 9/1996 | Herskowitz | 604/141 |
| 5,584,811 A | 12/1996 | Ross et al. | 604/141 |
| 5,597,042 A | 1/1997 | Tubel et al. | 166/250.01 |
| 5,624,409 A | 4/1997 | Seale | 604/246 |
| RE35,501 E | 5/1997 | Ross et al. | 604/141 |
| 5,743,878 A | 4/1998 | Ross et al. | 604/131 |
| 5,769,608 A | 6/1998 | Seale | 417/53 |
| 5,788,674 A | 8/1998 | McWilliams | 604/141 |
| 6,275,284 B1 | 8/2001 | Kiel et al. | 356/28 |
| 6,398,760 B1 | 6/2002 | Danby | 604/132 |
| 6,461,323 B2 | 10/2002 | Fowler et al. | 604/67 |

(Continued)

FOREIGN PATENT DOCUMENTS

WO   WO2007/098265 A2   8/2007

(Continued)

OTHER PUBLICATIONS

International Search Report and Written Opinion of the International Searching Authority dated Dec. 4, 2007, received in PCT/US2007/05095.

(Continued)

*Primary Examiner* — Hezron Williams
*Assistant Examiner* — Tamiko D Bellamy
(74) *Attorney, Agent, or Firm* — McLane, Graf, Raulerson & Middleton, Professional Association

(57) ABSTRACT

A method and apparatus are disclosed for using an acceleration of a flow control system to determine the density of a fluid relative to the density of an in-line flow object.

15 Claims, 7 Drawing Sheets

U.S. PATENT DOCUMENTS

| | | | |
|---|---|---|---|
| 6,641,562 B1 | 11/2003 | Peterson | 604/141 |
| 6,642,999 B2 | 11/2003 | Arndt et al. | 356/38 |
| 6,685,668 B1 | 2/2004 | Cho et al. | 604/65 |
| 6,981,960 B2 | 1/2006 | Cho et al. | 604/65 |
| 7,503,903 B2 | 3/2009 | Carlisle et al. | 604/67 |
| 7,654,982 B2 * | 2/2010 | Carlisle et al. | 604/132 |
| 2005/0235733 A1 | 10/2005 | Holst et al. | 73/1.16 |

FOREIGN PATENT DOCUMENTS

| | | |
|---|---|---|
| WO | WO2007/098287 A2 | 8/2007 |
| WO | WO2007/106232 A2 | 9/2007 |

OTHER PUBLICATIONS

International Search Report and Written Opinion of the International Searching Authority dated Apr. 1, 2008, received in PCT/US2007/04945.

International Search Report and Written Opinion of the International Searching Authority dated Sep. 11, 2008, received in PCT/US2007/02039.

* cited by examiner

DENSITY ANALYSIS FOR FLOW SENSOR-BASED FLUID CONTROL SYSTEM

CROSS-REFERENCE TO RELATED APPLICATIONS

This application is a continuation-in-part of U.S. patent application Ser. No. 12/048,612, filed Mar. 14, 2008, now pending. The aforementioned application is incorporated herein by reference in its entirety.

BACKGROUND

The present disclosure relates to fluid flow control systems, such as intravenous infusion pumps, and more particularly to feedback control infusion pumps with flow sensing, volume sensing, variable pressure control, and variable flow resistance. In particular, the present disclosure relates to a method and apparatus for extracting enhanced information from an in-line fluid flow sensor.

A conventional, large volume infusion pump is typically equipped with a motor that, in connection with a mechanical assembly and through the interface of a fluid barrier, pushes a small amount of fluid per motor "step." The mechanism might be a cam, a leadscrew, or other such assembly. The fluid barrier might be a syringe, an extruded tube, a molded cassette, or other such device that separates the pumping mechanism from the fluid in question. In each case, the fluid movement is determined by a certain number of motor steps over time.

At slow flow rates, the motor steps are relatively infrequent with long dwell periods. At high flow rates, the motor and mechanism are run at their maximal capacity until one element has reached its engineering limit. The flow rate is inherently pulsatile, yet this pulsatile nature is less significant at higher flow rates where the natural compliance of the outlet of the pumps serves to dampen the pulses into more or less a continuous stream of fluid.

The motors used conventionally are inherently powerful enough to overcome significant forces and resistances, so they are capable of generating significant pumping forces. This forceful pumping is an artifact and has no desirable clinical effect. The sensing mechanisms commonly used are pressure based and are made with indirect contact with the fluid to be pumped. In most cases, the fluid barrier, such as an extruded tube, exerts far more force than the internal fluid pressures. The result is a lack of sensitivity to pressure changes and a lack of feedback as to the actual conditions of fluid flow. It is common for conventional pumps to operate indefinitely without recognizing that the actual fluid flow rate is far below the targeted level.

Conventional motor driven pumps are notoriously inefficient with respect to external power consumption. For devices that have a high requirement for portability, this power inefficiency translates into unreliable operation.

Prior to the use of pumps, most infusions were done by the adjustment of a gravity-based pressure (e.g., by adjusting the height of a fluid container) and the adjustment of inline resistance (e.g., by moving the position of a roller clamp), both in response to an inline flow sensing method (e.g., performed by a user counting drops into an air chamber). Although this prior art method was labor intensive and had a limited rate range, it offered some significant advantages over the subsequent "advances" in technology. First, the use of gravity head heights for a delivery pressure was energy efficient. No external power supply was required. Second, the pressure was low, so the dangers of high-pressure infusions were avoided. Third, the gravity infusions could be augmented with a low cost and readily available pressure cuff, supplementing the fluid flow to rates well above those possible by an instrumented "pump" line. Forth, a gravity administration was not capable of infusing large amounts of air into the output line, because the hydrostatic pressure goes to zero as the fluid source empties.

An ideal infusion system will combine the meritorious aspects of a conventional "gravity" infusion with the benefits of a controlled intravenous infusion pump. In each aspect, this disclosure takes the desired principles of a gravity infusion and reduces the dependence upon skilled labor and extends the range and precision of fluid flow control and provides advanced information management capabilities.

An ideal embodiment of an infusion device would be one with continuous flow, wide flow rate range, high energy efficiency, accuracy of volume delivered over time, minimal operating pressures, maximum sensitivity to external conditions, freedom from false alarms for air-in-line, simplicity, low cost, intuitive operation, automated information exchange, safety, and reliability.

Certain infusions have historically been managed by air pressure delivery systems, most commonly found in the operating room and in emergency situations. Prior art attempts have been made to determine the flow rate via pressure monitoring and control. For example, U.S. Pat. No. 5,207,645 to Ross et al. discloses pressurizing an IV bag and monitoring pressure to infer flow rates. However, the prior art systems lack independent flow sensing and, therefore, do not offer enough information to provide accurate and safe infusions.

Even under the best of circumstances, there is not enough information in a pressure signal alone to provide the accuracy needed for intravenous infusion therapy. Furthermore, there are a number of likely failure modes that would go undetected using the pressure signal alone. An infusion pump must be able to respond to events in a relevant time frame. International standards suggest that a maximum period of 20 seconds can lapse before fluid delivery is considered "non-continuous." As an example, for an infusion of 10 ml/h, the system would want to resolve 20 seconds of flow, which corresponds to 0.056 mL. This volume represents one part in 18,000 of air volume of a 1,000 mL bladder. Temperature induced change in pressure brought about by a normal air conditioning cycle is far greater than this signal. The measurement of pressure alone, therefore, is not adequate for an intravenous infusion device. No general purpose, full range, infusion devices using pressure-controlled delivery are known to be on the market.

An entire class of "passive" infusion pumps exists whereby a constant pressure is created on a fluid filled container by way of a spring, elastomeric structure, gas producing chemical equilibrium, or other means. This constant pressure fluid is fed into a high resistance output line, providing relatively stable fluid flow.

In typical pressure based flow control products, a relatively high pressure pushes fluid into a known, high, and fixed resistance, providing a constant flow rate with good immunity from changes in external conditions. It is a purpose of our prior commonly owned provisional application Ser. No. 60/777,193, filed on Feb. 27, 2006, and PCT Publication Nos. WO2007/098287, WO2007/098265, and WO2007/106232 to provide a highly flexible flow control system with a very broad flow rate range, operating under minimal pressures, with a relatively low and variable resistance. The entire contents of the aforementioned provisional and PCT applications are incorporated herein by reference.

Embodiments of such devices control fluid flow based on a responsive fluid flow sensing means that forms a closed loop control by changing both the fluid driving pressure and the inline resistance. In contrast to the conventional approach to flow control wherein a user observes fluid flowing as it forms drops in an air chamber, then adjusts pressure by varying the head height of the fluid source, and then adjusts the inline resistance via a manual valve, our above-mentioned disclosures employ a flow sensing apparatus and method that automatically and accurately measures fluid flow rate, precisely adjusts the hydrostatic pressure of the fluid source, and precisely adjusts inline fluid flow resistance to achieve or maintain a target flow rate.

The present disclosure contemplates a new and improved flow control system and method.

SUMMARY

Certain embodiments of an in-line fluid flow sensor are based on the position of a movable object in the flow path in which the force of the fluid flow is balanced by an opposing force. The resultant equilibrium position is a function of the fluid flow rate and of the fluid viscosity being measured.

The present disclosure describes an apparatus and method of enhancing the information derived from such an in-line fluid flow sensor by examining its response to forces of acceleration. The response of the fluid flow sensor can provide additional information, such as the density of the fluid relative to the density of the flow object.

The force that opposes fluid flow may be comprised of multiple elements. In one embodiment, a spring element, such as a coiled metal compression spring or other resiliently compressible member, presses against a flow object, such as a sphere, cylinder, or the like. The force of the spring, in opposition to the force of fluid flow, is added to the component of the buoyancy force on the flow object along the flow axis to provide a net opposing force on the flow object. If the axis of movement for the flow object is in perfect alignment with an acceleration, such as gravity, then the full force of the buoyancy of the object is added to the spring force. If the axis of movement for the flow object is orthogonal to an acceleration, such as gravity, then none of the force of the buoyancy of the object is added to the spring force.

In certain embodiments of a fluid flow sensor, a signal can be analyzed to determine the position of an object in the flow path. The flow object may alter its position as a result of a change in the flow rate change and/or a change in the opposing force. The flow object, having an associated and well-known mass, will experience an acceleration if a force is applied. The flow object is surrounded by an infusion fluid. If the flow object has the exact same density as the surrounding fluid, then the flow object will see forces in perfect synchrony with the infusion fluid when the flow sensor undergoes an acceleration. In other words, there will be no relative motion between the flow object and the infusion fluid. If, however, the flow object has a density that is substantially different from the infusion fluid, then an acceleration will create a differential force on the flow object relative to the liquid and, if unconstrained, the flow object will move relative to the infusion fluid.

As an example, if a heavy object is connected to and sitting on top of a spring, it will reach a certain equilibrium position. If the system is turned upside down, reversing the acceleration forces of gravity, the object will achieve a new equilibrium position. The weight of the object is either added to or subtracted from the force of the spring, depending on the gravitational orientation.

Gravity is one form of acceleration that may alter the net force on the flow object and, therefore, its equilibrium position. Any movement of the flow system will apply these forces to the flow object and the surrounding infusion fluid.

If the response of an independent sensor of acceleration can be compared to the positional readings from the optical flow sensor, then the relative density of the flow object and the surrounding infusion fluid can be measured. Since the material and density of the flow object and the biasing spring force-displacement response are known, then the density of the unknown infusion fluid can be inferred.

The flow object in the embodiments depicted herein is constrained along a single axis. Thus, only accelerations along this flow axis can be observed. Any acceleration along the other two mutually orthogonal axes will not produce a change in the flow object position and does not provide an insight into the density of the infusion fluid. In actual practice, a device that includes the flow sensor is likely to experience nearly random acceleration, some of which will result in an acceleration vector along the axis of measurement.

The value of detecting the fluid density, especially when coupled with the ability to measure properties of viscosity, optical reflectance, optical refraction, and optical absorption may be helpful in characterizing the infusion fluid. For example, it may be a valuable patient safety feature to identify the infusion of whole blood, as compared to the infusion of low density fluids.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
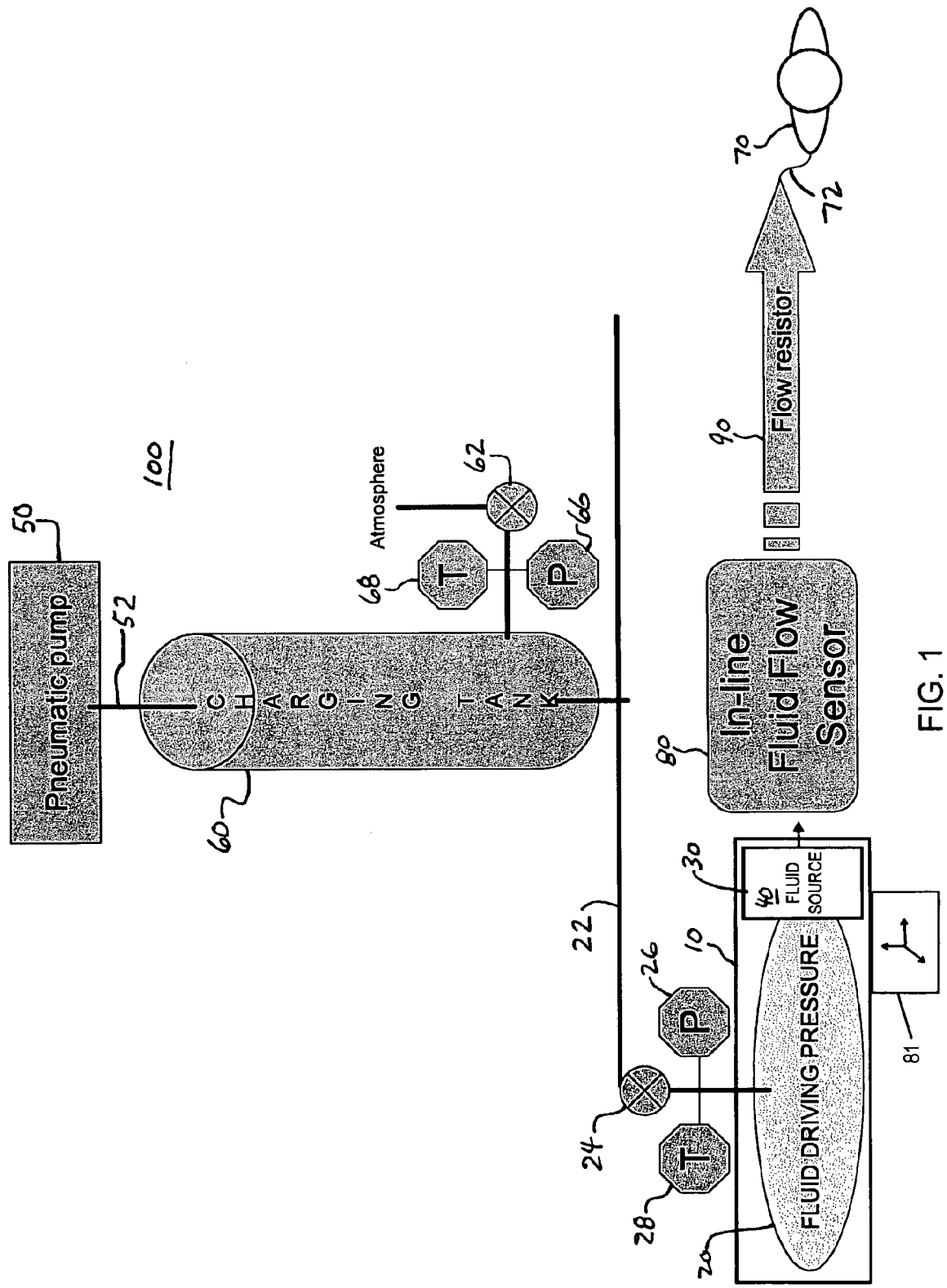
FIG. 1 is a functional block diagram of a fluid pumping system operable to embody an exemplary embodiment of the present invention.

Referring to the drawings, FIG. 1 depicts an exemplary flow control system 100 in accordance with an exemplary embodiment of the present disclosure. The system includes a pressure frame 10 that is of known total volume and contains within it an air bladder 20 and a flexible bag 30 that contains within it a liquid 40 to be delivered. A 3-axis accelerometer 81 is attached to the exterior of pressure frame 10 to detect and output a signal representative of acceleration experienced by flow control system 100. Alternatively, the accelerometer 81 may be a single axis accelerometer that is aligned with the direction of fluid flow, which is sufficient to measure the component of acceleration that is parallel to the direction of fluid flow.

The air bladder 20 is connected to a charging tank 60 of known volume via a conduit or line 22 extending between an outlet of the tank 60 and an inlet of the bladder 20. A pneumatic pump 50 is pneumatically coupled to an inlet of the charging tank 60 via a line 52. A bladder valve 24 in the line 22 may be selectively opened and closed to selectively couple and decouple the outlet of the tank 60 with the inlet of the bladder 20. The charging tank may selectively be vented to atmosphere via a tank vent valve 62. The air bladder 20 may be vented to atmosphere via an optional bladder vent valve (not shown). Alternatively, the bladder 20 may be vented to atmosphere by opening the valves 24 and 62.

The tank 60 is connected to a tank pressure sensor 66 and a tank temperature sensor 68. The bladder 20 is connected to a bladder pressure sensor 26 and a bladder temperature sensor 28.

The fluid 40 is fluidically coupled to an output 70 via an inline flow sensor 80, a fluid flow resistor 90, and an output line 72. The fluid 40 may be, for example, a medication fluid, intravenous solution, blood product, or the like, to be infused and the output 70 may be, for example, a patient or subject in need thereof In the depicted embodiment of FIG. 1, the flow resistor 90 is shown downstream of the in-line flow sensor 80. Alternatively, the flow resistor 90 may be positioned upstream of the flow sensor 80. The flow resistor 90 and flow sensor 80 may be separate or may be integrally formed.

Figure 2:
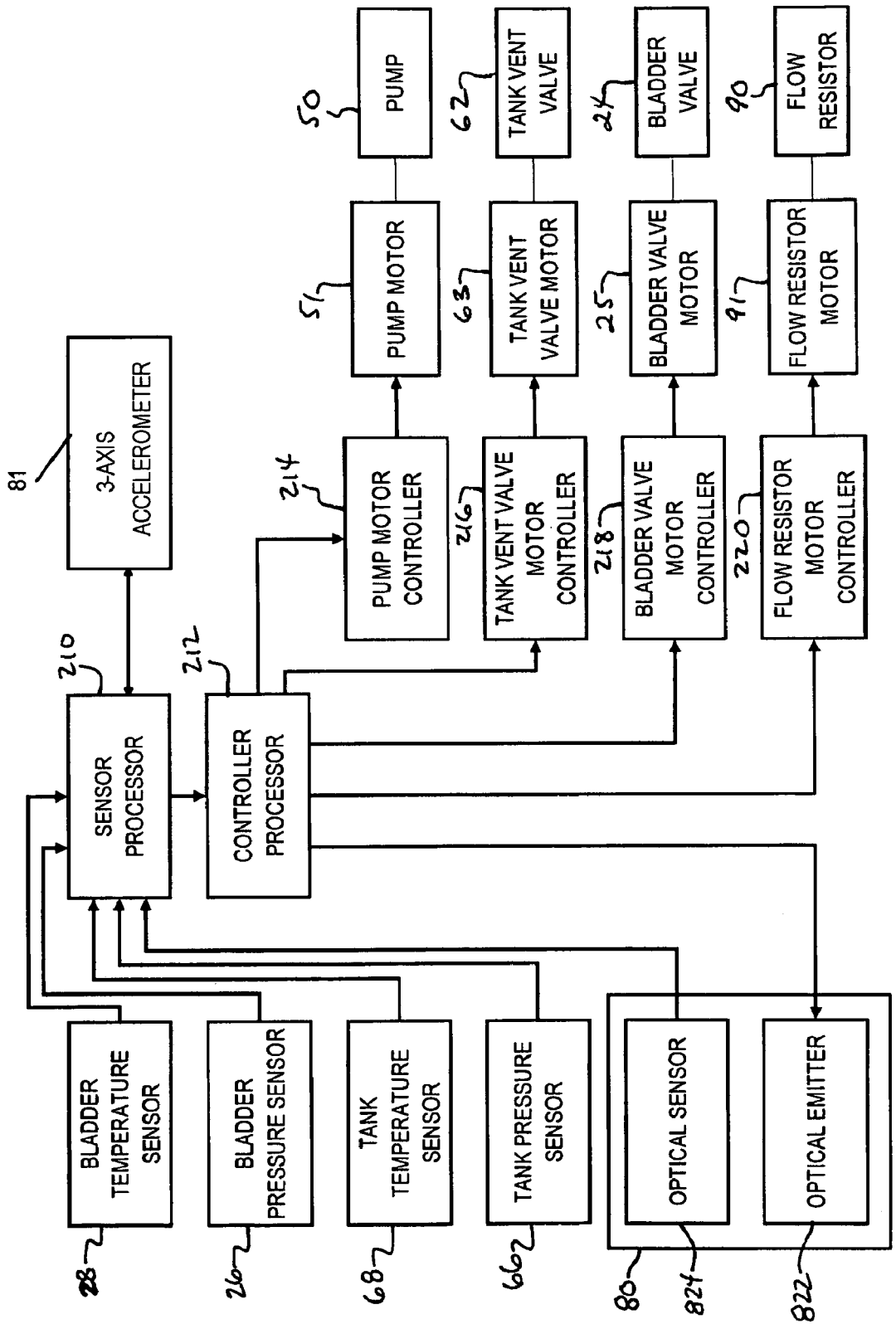
FIG. 2 is a functional block diagram of a flow sensor and control circuit for the system appearing in FIG. 1.

In reference to FIG. 2, an embodiment of the fluid control system 100 includes the pump 50 including a pump motor 51, the bladder valve 24 including a bladder valve motor 25, the tank vent valve 62 including a tank vent valve motor 63, the flow sensor 80 including an optical sensor 824 and an optical emitter 822, the flow resistor 90 including a flow resistor motor 91, the tank pressure sensor 66, the tank temperature sensor 68, the bladder pressure sensor 26, the bladder temperature sensor 28, a sensor processor 210, a controller processor 212, the accelerometer 81, a pump motor controller 214, a tank vent valve motor controller 216, a bladder valve motor controller 218, and a flow resistor motor controller 220.

The sensor processor 210, controller processor 212, pump motor controller 214, tank vent valve motor controller 216, bladder valve motor controller 218, and flow resistor motor controller 220 may be implemented in a microprocessor, microcontroller, controller, embedded controller, or the like. Although the processors 210 and 212 and the controllers 214-220 are depicted in FIG. 2 as discrete modules or processors for conceptual simplicity and ease of exposition, it is to be appreciated that modules 210-214 can share common hardware. Well-known internal components for processing and control modules, such as power supplies, analog-to-digital converters, clock circuitry, etc., are not shown in FIG. 2 for simplicity and would be understood by persons skilled in the art.

The controller processor 212 controls the pump 50 via the pump motor controller 214, the tank vent valve 62 via the tank vent valve controller 216, the bladder valve 24 via the bladder valve controller 218, and the flow resistor 90 via the flow resistor motor controller 220. Alternatively, the controller processor 212 may control one or more of the motors directly or via any other suitable known device. The controller 212 may also control the application of power to the optical emitter 822.

The sensor processor 210 receives a signal indicative of bladder temperature and pressure from the bladder temperature sensor 28 and bladder pressure sensor 26, respectively. The sensor processor 210 receives a signal indicative of tank temperature and pressure from the tank temperature sensor 68 and tank pressure sensor 66, respectively. The sensor processor 210 receives a signal from the optical sensor 824 indicative of the position of a flow sensor indicator element in the flow path as described below. The sensor processor 210 also receives a signal from the accelerometer 81 indicative of the forces exerted on the accelerometer 81. It will be recognized that the accelerometer 81 may be located on the flow sensor 80, or may be located elsewhere on the flow control system 10, such as on the pressure frame 10. Preferably, the accelerometer 81 is attached to the pressure frame 10 in close proximity to the flow sensor element 80 such that accelerations experienced by the accelerometer 81 will approximate the accelerations experienced by the flow sensor 80 and flow object 818.

Figure 3:
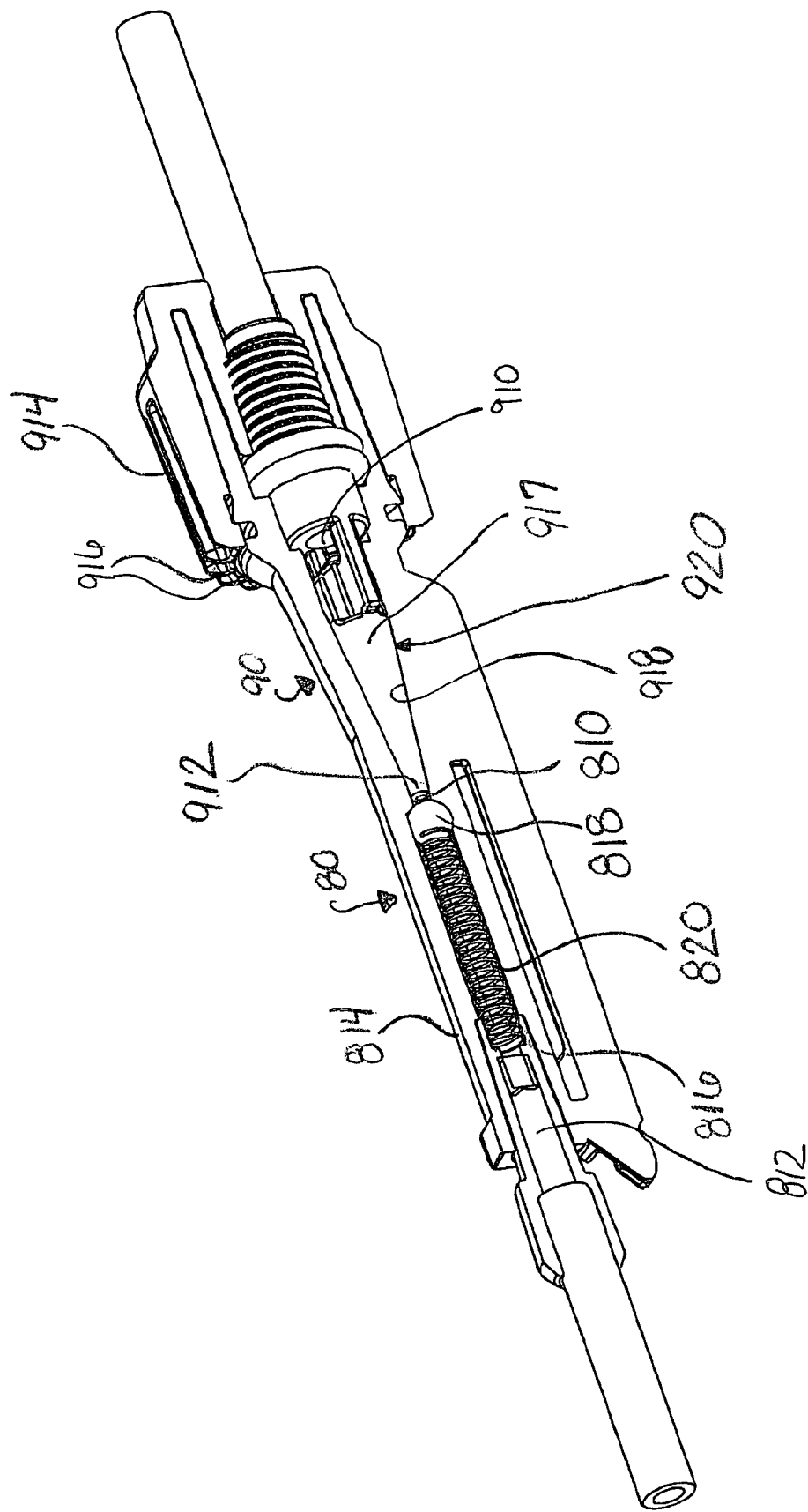
FIG. 3 is an isometric sectional view illustrating an exemplary flow sensor with integral resistor element.

FIG. 3 shows an exemplary flow sensor 80 with integral flow resistor 90. The flow resistor 90 includes an inlet end 910 fluidly coupled to the fluid source 40 and an outlet 912 fluidly coupled to an inlet 810 of the flow sensor 80. The flow sensor 80 includes an outlet end 812 fluidly coupled to the output 50 such as the vasculature of a patient, e.g., via an IV catheter or cannula as generally known in the art. Although the inline sensor 80 and the flow restrictor 90 are depicted as an integral assembly in the embodiment of FIGS. 3 and 4A-4C, it will be recognized that the flow resistor and the flow sensor units may be discrete assemblies fluidically coupled in serial fashion.

In reference to FIGS. 3 and 4A-4C, the flow resistor 90 includes a rotatable housing 914, which may have a plurality of radially extending ribs or projections 916 forming a gear that may be selectively rotated by the motor 91, which may be a stepper motor having an intermeshing member, or the like. The rotatable housing 914 is coupled to an axially movable needle resistor 917 wherein rotating the housing 914 in one direction causes the needle resistor 917 to move in one axial direction and rotating the housing 914 in the opposite direction causes the needle resistor 917 to move in the opposite axial direction, for example, via helical threads formed on an interior surface of the rotatable housing member 914. As best seen in FIG. 3, the needle resistor axially moves between a first, closed position wherein the needle resistor engages a mating seat 918 and a fully open position. An annular gap 920 defined between the needle resistor 917 and the seat 918 increases as the valve moves from the closed position to the fully open position, thereby providing a variable flow resistance, which varies as a function of the degree of rotation of the housing 914.

The flow sensor 80 includes a housing portion 814 defining an axial channel or bore 816 receiving a flow object 818. The flow object 818 may be a spherical or cylindrical member. The preferred embodiment employs a cylindrical flow object. A spring member 820 urges the flow object 818 in a direction opposite to the direction of flow. The spring member 820 may be a coil spring (e.g., conical or cylindrical coil spring) or may be another resiliently compressible material such as a foam member, deflectable band or leaf spring, or the like.

The spring member 820 bears against the flow object 818 and applies a force to the flow object in the direction opposite to the direction of fluid flow. An adjustment mechanism, such as a threaded member engaging the fixed end of the spring 820 may be provided to axially advance or retract the fixed spring end to adjust the force preload of the spring 820 on the flow object 818. In operation, fluid flow will exert a force on the sensor flow object 818 against the urging of the spring 820, which force increases as the flow rate increases. The flow object 818 thus moves until an equilibrium position is reached such that the force of the compression spring 820 on the flow object 818 is balanced by the force of the fluid flow against the flow object 818. The direction and distance that the flow object moves in response to an acceleration of the flow sensor 80, is dependant on the density of the flow object relative to the density of the infusion fluid 40.

Figure 4A:
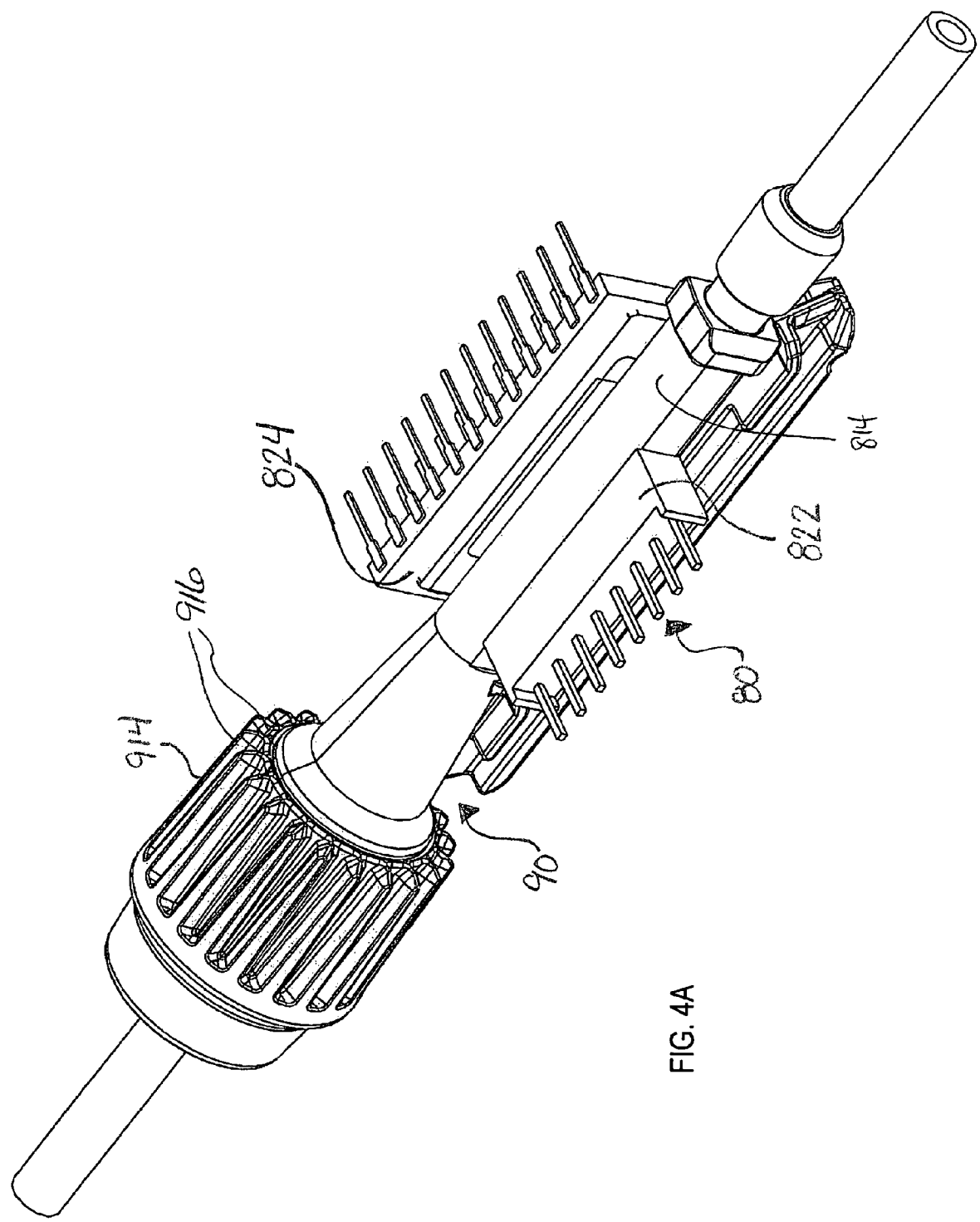
FIGS. 4A and 4B are isometric views of an exemplary flow sensor with integral resistor element, showing the optical emitter and receiver.
Figure 4B:
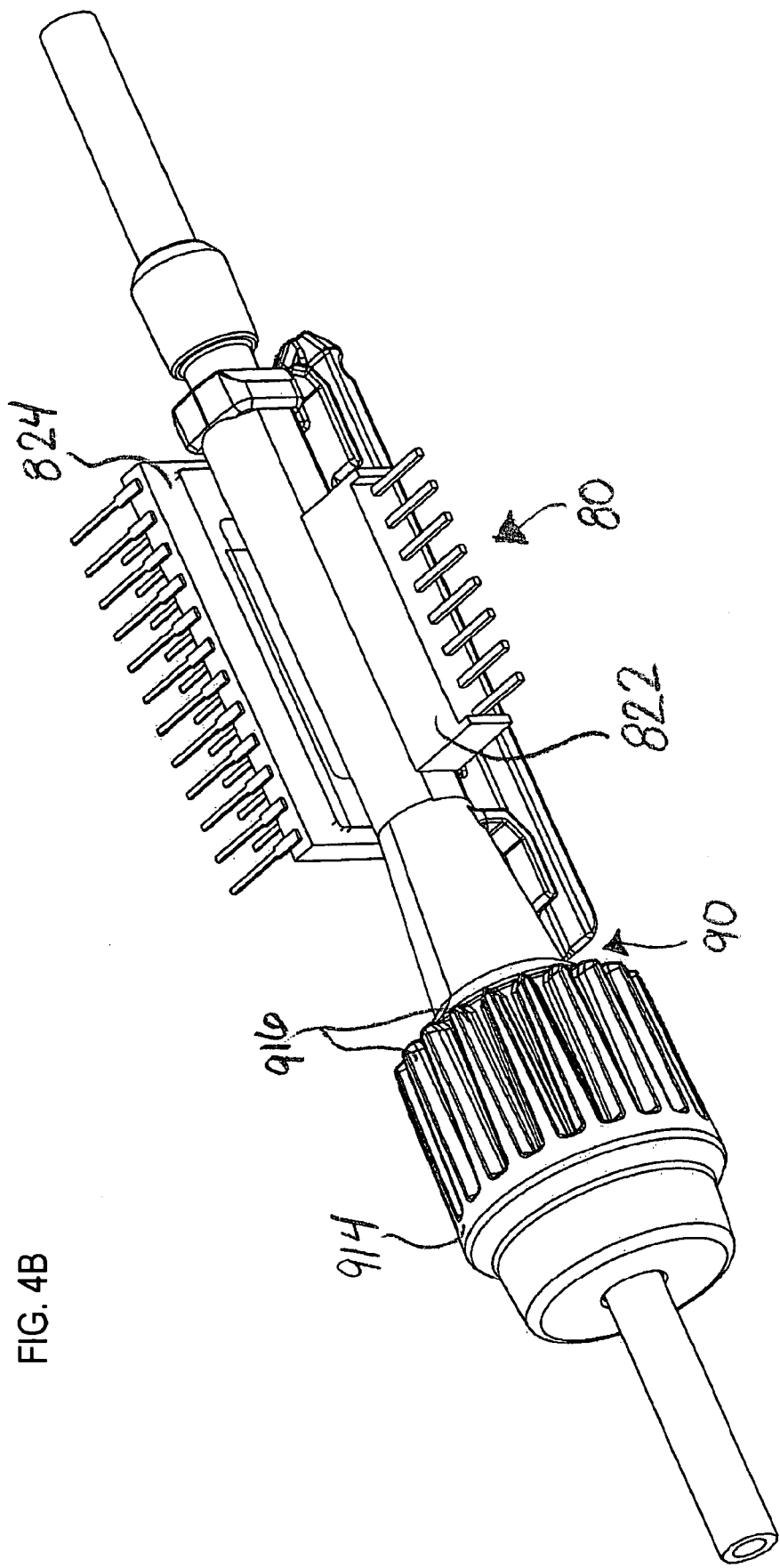
Figure 4C:
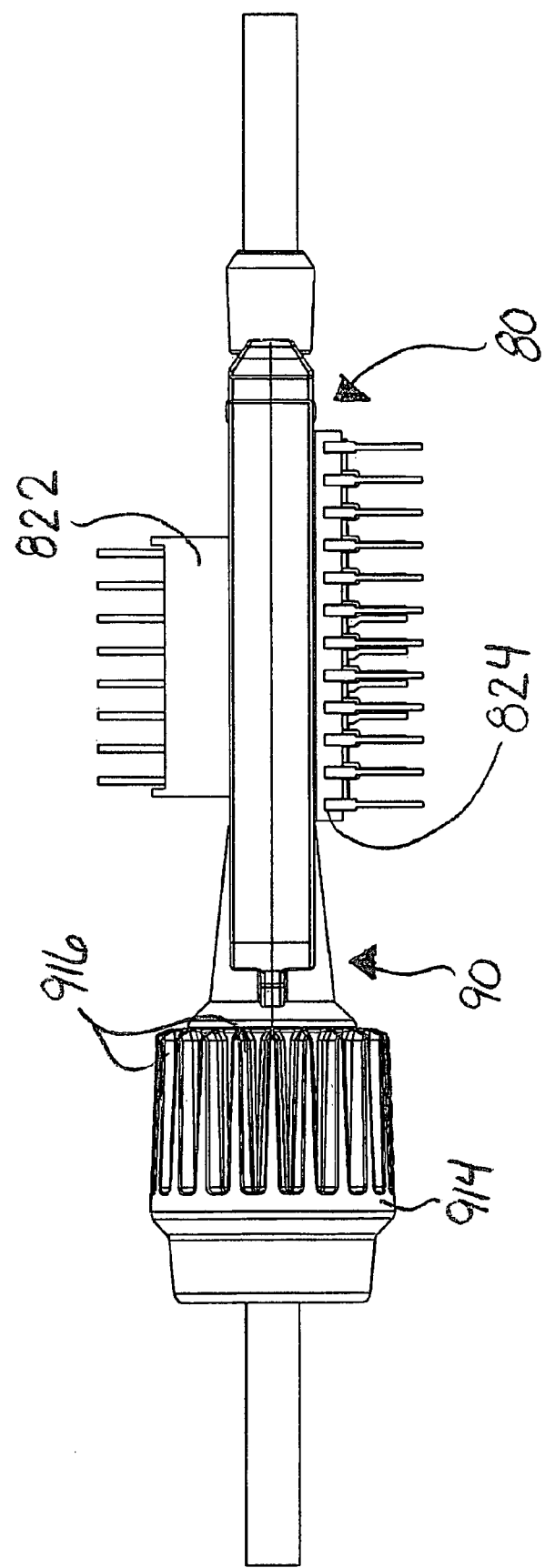
FIG. 4C is a side view of the flow sensor embodiment appearing in FIGS. 4A and 4B.

In reference to FIGS. 4A-4C, the optical emitter 822, which may be, for example, an LED array, organic light-emitting diode (OLED) array or a spectrophotometer, is provided on a first side of the housing 814 and the optical receiver 824, which may be, a photosensitive array, charge-coupled device (CCD) array, photodiode array, complimentary metal oxide semiconductor (CMOS) digital detector array, or the like, is provided on a second side of the housing 814 opposite the first side. The optical emitter 822 transmits light through the housing 814 and into the cavity 816. The light incident upon the flow object 818 is transmitted through the flow object 818 and opposite wall of the housing 814 to form a light intensity pattern on the optical sensor 824. Where the fluid flowing through the channel 816 is a generally opaque fluid or otherwise has a high absorbance of the light emitted by the emitter 822, the flow object 818 may be a clear flow object, e.g., formed of acrylic or other transparent polymeric material, which serves to dramatically reduce the optical path length of the fluid in the optical path between the emitter 822 and the sensor 824 in the vicinity of the flow object 818, thereby reducing the absorption of light by the fluid surrounding the flow object in the flow passageway. Also, the use of a clear flow object 818 allows the flow object to function as a lens to transmit and focus the light.

The optical transmitter 822 may include one or more light source elements having a wavelength, for example, in the infrared (IR), visible, or ultraviolet (UV) region and the housing and flow object may be formed of a material that optically transmits light of the light source wavelength. The light source 822 may be an array of light elements, such as LEDs, or laser, etc. The light source may be segmented or continuous along the flow axis. The light source may be a physical array of light elements or may be a beam scanned or otherwise optically formed along the length of the optical detector. The light source may illuminate the detector array along its length simultaneously or by sequentially scanning along its length. The refractive effect of a transparent flow object, e.g., a transparent sphere or cylinder, may have a focusing effect on the light passing therethrough that may be detected by the photosensor array.

Alternatively, a nontransmissive flow object 818 may be employed and the flow object position may be determined by detecting the position of a shadow cast by the flow object on the photosensor array. In still further embodiments, the flow object member may have a reflective surface and the optical sensor array may be positioned to detect light emitted from the light source 822 and reflected from the surface of the flow object. Other embodiments may use contact image sensors (CIS), which include both emitters and detectors, whereby the emitted light source is parallel to the detectors allowing the reflected signal to be sensed by the detectors. In still other embodiments, multiple wavelength LED or OLED arrays may be used to transmit red, green and blue wavelengths to the optical receiver which absorbs the received wavelengths and provides additional information for determining the type of infusion fluid being administered.

The output from the photosensitive array is a set of pixel voltage values which vary in accordance with the amount of light impinging on the each pixel of the photosensitive array. The pixel voltage values may be sampled and digitized using an analog-to-digital converter and stored as digital data in an electronic storage medium as a numerical representation of the pixel output voltage levels, and thus, light intensity levels, along the detector array.

The output of the optical sensor 824 may be passed to the sensor processor 210, which may include a position-detection module or circuitry wherein the axial position of the flow object 818 within the channel 816 is determined. The axial position of the flow object 818 may in turn be used to determine a flow rate and/or calibrate or correlate flow object positions with known flow rates calculated by other means such as plural volume measurements made using the methods outlined in the aforementioned U.S. provisional application Ser. No. 60/777,193 and PCT Publication Nos. WO2007/098287, WO2007/098265, or WO2007/106232.

The axial position of the flow object 818 is monitored to determine the direction of movement, if any, of the flow object in response to an acceleration and, preferably, the distance traveled by the flow object 818 in response to an acceleration of the flow sensor 80, as measured by the accelerometer 81. The direction and distance traveled by the flow object 818 in response to a sensed acceleration may be used to determine the density of the fluid 40 relative to the density of the flow object 818, which is of known density.

When the direction of flow object 818 movement and optionally the distance traveled is determined, the density of the fluid 40 relative to the density of the flow object 818 can be inferred. Once the relative density of the fluid is determined based on flow object movement in response to acceleration, it may be compared for consistency with the known density for the fluid that was ordered to be delivered to the patient. This comparison can be done in a number of ways including a chart look up, an electronic database, etc. If the inferred density of the fluid 40 actually being delivered to a patient is inconsistent with a known density of the fluid that was ordered to be delivered to the patient, an alarm, such as an audio and/or visual alarm output, may be provided to alert the user of the inconsistency. Thus, comparing the inferred relative density of the fluid 40 being delivered to a known density of the ordered fluid acts as an additional safeguard to ensure that the patient is receiving the correct infusion fluid 40.

Figure 5:
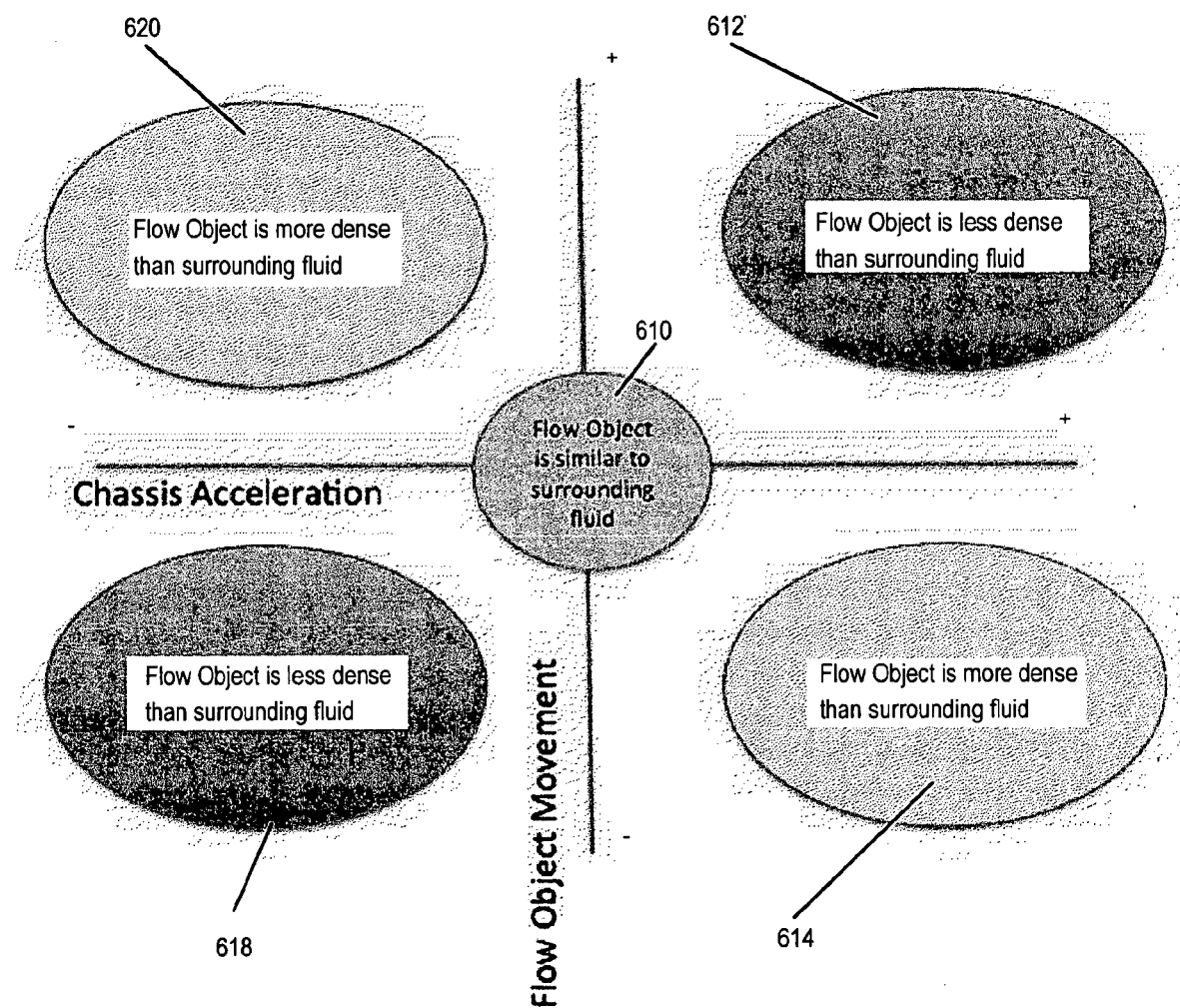
FIG. 5 is a graph of chassis acceleration versus flow object movement for determining the relative density of the infusion fluid.

Referring now to FIG. 5, there appears a graph of flow object movement as a function of chassis acceleration. Accelerations of the flow sensor 80 may be created when the unit is moved, e.g., by the patient, health care workers, etc. In the depicted preferred embodiment, the flow sensor 80 is integral with the flow control system 100 and acceleration of the flow sensor 80 may be created by movement of the pressure frame 10. These movements causing acceleration may be intentional or unintentional.

When the pressure frame 10 is moved, the sensor unit 80 and the accelerometer 81 experience an acceleration. A signal representative of the acceleration is output by the accelerometer 81, which may be sampled and stored as a digital representation of the acceleration, e.g., by the sensor processor 210. When the accelerometer 81 experiences an acceleration, the flow object 818 may also move, depending on the component of acceleration in the flow direction and the density of the sensor element 818 relative to the fluid 40. If the accelerometer 81 is a single-axis accelerometer aligned with the direction of fluid flow, then the acceleration signal will be representative of the acceleration along the flow axis. If the accelerometer is a multi axis accelerometer, then the component of acceleration in the flow direction is calculated.

If the accelerometer 81 experiences an acceleration in either the positive or negative direction relative to the direction of fluid flow, and the flow object remains in substantially the same position 610, then it is inferred that the density of the infusion fluid 40 is substantially the same as the known density of the flow object 818.

If the accelerometer 81 experiences an acceleration in the positive direction relative to the direction of fluid flow, and the flow object moves in a positive direction 612 in response thereto, then it is inferred that the density of the infusion fluid 40 is greater than the known density of the flow object 818.

If the accelerometer 81 experiences an acceleration in the positive direction relative to the direction of fluid flow, and the flow object moves in a negative direction 614 in response thereto, then it is inferred that the density of the infusion fluid 40 is less than the known density of the flow object 818. Thus, while the distance of the flow object movement may provide additional information about the degree of difference between the flow object and the fluid 40, it will be recognized that the present disclosure does not require a quantitative determination of the density of the fluid 40.

If the accelerometer 81 experiences an acceleration in the negative direction relative to the direction of fluid flow, and the flow object moves in a positive direction 620 in response thereto, then it is inferred that the density of the infusion fluid 40 is less than the known density of the flow object 818.

If the accelerometer 81 experiences an acceleration in the negative direction relative to the direction of fluid flow, and the flow object moves in a negative direction 618 in response thereto, then it is inferred that the density of the infusion fluid 40 is greater than the known density of the flow object 818.

Thus, the direction in which the flow object 818 travels indicates whether the relative density of the fluid 40 is greater than or less than the known density of the flow object 818. Furthermore, the magnitude of the change in position of the sensor element under acceleration in response to an acceleration is proportional to the magnitude of the difference between the density of the fluid 40 and the known density of the sensor element 818.

In operation, an abrupt change in flow rate is caused by the movement of flow control system 100, thereby introducing an acceleration on the flow object 818, the accelerometer 81, and the fluid 40. The movement of the flow control system 100 can either be an intentional movement, e.g., by a physician or nurse, or may be an accidental or unintentional movement, e.g., created by the movement of the patient. The axial position of the sensor flow object 818 is monitored as a function of time, and is correlated with the acceleration component in the flow direction sensed by the accelerometer during the acceleration, until the flow object assumes a new equilibrium position.

While the direction of any resulting change in position of the flow object 818 is sufficient to determine whether the density of the liquid 40 is greater or less than the know density of the flow object 818, in preferred embodiments, one or both of the magnitude of the position change and the rate of position change of the flow sensor element is additionally calculated, e.g., by comparing flow object pixel position along the sensor array and/or by determining the average slope of position as a function of time for the period of time in which it took the flow object to move from its initial equilibrium position at the initial flow rate to its new equilibrium at the new flow rate.

The movement of the flow object 818 is monitored as an acceleration is exerted on the flow control system 100 until the flow object assumes a new equilibrium position. The accelerometer 81 monitors and records the accelerations experienced by the pressure frame 10. To determine the relative density of fluid 40 the direction of the flow object 818 movement is determined. Additional information about the magnitude of the difference between the fluid 40 density and the known flow object 818 density can be determined by the time it takes the flow object to reach a new equilibrium position and/or the rate at which the flow object moves when the biasing spring force-displacement response is also known.

The relative density of the fluid 40 as determined above may be checked against an expected fluid density, which may be a known density of the fluid ordered or prescribed to be delivered to the patient. For example, the type of fluid 40 to be infused may be input into the flow control system, e.g., by the operator using a user interface of the processor 210 and/or 212. Alternatively, the type of fluid 40 may be identified by reading a bar code (or other optically readable indicia) or radio frequency identification (RFID) tag on or in the fluid container, e.g., by a bar code (optical) scanner or RFID scanner.

The relative density of the fluid 40 as determined above may then be checked to determine whether it is consistent with an expected fluid density based on prestored density characteristics associated with the fluid type input by the operator (e.g., stored in a database, lookup table, data file, memory, etc.). For example, in the case of IV infusion fluids, many fluids or at least categories of fluids, such as blood products (e.g., whole blood, platelets, plasma, immunoglobulins, packed red cells etc.), saline, dextrose, albumin, lactated ringers solution, amino acids, lipid emulsions, parenteral nutritional solutions, etc., will have different densities. If the inferred density of the fluid 40 relative to the known density of the flow object 818 is different from the expected density of the fluid, the operator may be alerted to this potential error condition, thereby providing an additional safeguard. Such alarm or alert may be, for example, an audible alarm, a visual alarm such as a light or on-screen display, an alarm message transmitted via a computer network or communications network, a somatic alarm, and so forth.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof

Having thus described the preferred embodiments, the invention is now claimed to be:

1. A method for determining a density of a fluid relative to a density of a flow object in a flow control system of a type having a flow rate sensor including the flow object movably received in an axially extending flow passageway, the flow object being axially movable within the flow passageway in response to a first force exerted on the flow object by the fluid as it passes through the flow passageway and a second force exerted on the flow object in a direction opposite the first force by a spring member received within the flow passageway, the flow object reaching an equilibrium position within the flow passageway when the first and second forces are equal, the equilibrium position corresponding to an axial position within the flow passageway which varies with varying flow rate, said method comprising:

sensing an acceleration of the flow rate sensor with an accelerometer;

monitoring a change in position of the flow object responsive to the acceleration;

determining a direction of movement of the flow object; and determining the relative density of the fluid relative to the flow object.

2. The method of claim 1, wherein said step of determining the density of the fluid relative to the density of the flow object includes determining whether the density of the fluid is equal to, greater than, or less than the density of the flow object.

3. The method of claim 1, further comprising:

prior to sensing the acceleration, causing a movement of the flow rate sensor.

4. The method of claim 1, wherein the acceleration is sensed using a three-axis accelerometer and wherein the relative density is sensed using a component of the acceleration which is a parallel to a direction of fluid flow in the flow passageway.

5. The method of claim 1, wherein the acceleration is sensed using a single-axis accelerometer which is oriented to sense acceleration in a direction parallel to a direction of fluid flow in the flow passageway.

6. The method of claim 1, wherein the density of the flow object is known.

7. The method of claim 6, further comprising:
determining a magnitude of the change in position of the flow object responsive to the acceleration, wherein said magnitude of the change in position is proportional to a magnitude of the difference between the density of the flow object and the density of the fluid.

8. The method of claim 1, further comprising:
inputting fluid density information including an expected density of the fluid;
comparing the relative density of the fluid to the expected density of the fluid; and
if the relative density of the fluid is inconsistent with the expected density, of the fluid, generating an alert.

9. The method of claim 1, further comprising:
if the flow object does not move responsive to a sensed acceleration, inferring that the density of the fluid is substantially the same as the density of the flow object;
if the flow object moves in a direction of fluid flow responsive to an acceleration of the flow rate sensor in the direction of fluid flow, inferring that the density of the fluid is greater than the density of the flow object;
if the flow object moves in a direction opposite the direction of fluid flow responsive to an acceleration of the flow rate sensor in the direction of fluid flow, inferring that the density of the fluid is less than the density of the flow object;
if the flow object moves in the direction of fluid flow responsive to an acceleration of the flow rate sensor in the direction opposite the direction of fluid flow, inferring that the density of the fluid is less than the density of the flow object; and
if the flow object moves in the direction opposite the direction of fluid flow responsive to an acceleration of the flow rate sensor in the direction opposite the direction of fluid flow, inferring that the density of the fluid is greater than the density of the flow object.

10. The method of claim 1, wherein the fluid is an intravenous infusion fluid.

11. The method of claim 1, further comprising:
passing light from a light source in a direction that is perpendicular to the direction of fluid flow in the passageway;
sensing the light from the light source passing through the flow passageway using a light sensor;
determining a wavelength of the light sensed by the light sensor; and
determining the fluid in the flow passageway based on the wavelength.

12. An apparatus for determining a density of a fluid relative to a density of a flow object in a flow control system, said apparatus comprising:
a flow sensor for fluidic coupling between a source of the fluid and a target object for receiving the fluid, said flow sensor including the flow object movably received within an axially extending flow passageway and an optical sensor for monitoring an axial position of the flow object within the axially extending flow passageway and for generating a signal representative of the axial position of the flow object in the flow passageway;
an accelerometer coupled to the flow control system for generating a signal representative of an acceleration of the flow sensor; and
a processor operably coupled to the accelerometer and the optical sensor for receiving the signal from the optical sensor representative of the axial position of the flow object in the flow passageway and the signal from the accelerometer representative of the acceleration of the flow sensor and determining the density of the fluid relative to the density of the flow object.

13. The apparatus of claim 12, wherein said fluid is an intravenous infusion fluid.

14. The apparatus of claim 12, wherein the flow object is selected from a cylindrical flow object and a spherical flow object.

15. A method for inferring density of a fluid in a flow control system, the flow control system controlling a flow of the fluid, the flow control system having a flow passageway, a flow object movably positioned in the flow passageway and a sensor for sensing a position of the flow object in the flow passageway, wherein a position of the flow object in the flow passageway is responsive to a flow rate of the fluid in the flow passageway, further wherein the flow rate is responsive to a fluid driving pressure and a systematic flow resistance in the flow control system, said method comprising:
causing movement of the flow control system to impart an acceleration to the flow control system;
measuring an acceleration experienced by the flow object with an accelerometer attached to the flow control system;
monitoring the position of the flow object in the flow passageway and calculating any one or both of: (a) a direction of movement of the flow object in the flow passageway responsive to the acceleration; and (b) a direction and distance of movement of the flow object in the flow passageway responsive to the acceleration; and
inferring a density of the fluid relative to a known density of the flow object.

* * * * *